(12) United States Patent
Shen et al.

(10) Patent No.: US 8,476,057 B2
(45) Date of Patent: Jul. 2, 2013

(54) ANTAGONISTIC BACTERIA FOR PREVENTING AND ELIMINATING THE BACTERIAL WILT OF CONTINUOUS CROPPING TOBACCO AND THEIR MICROBIAL ORGANIC FERTILIZER

(75) Inventors: Qirong Shen, Nanjing (CN); Yanxia Liu, Nanjing (CN); Xingming Yang, Nanjing (CN); Yangchun Xu, Nanjing (CN); Biao Shen, Nanjing (CN)

(73) Assignees: Jiangsu New Ground Bio-Fertilizer Engineering Center Co., Ltd., Jiangsu (CN); Nanjing Agricultural University, Jiangsu (CN)

( * ) Notice: Subject to any disclaimer, the term of this patent is extended or adjusted under 35 U.S.C. 154(b) by 262 days.

(21) Appl. No.: 12/747,508

(22) PCT Filed: Nov. 17, 2009

(86) PCT No.: PCT/CN2009/074977
§ 371 (c)(1),
(2), (4) Date: Jun. 10, 2010

(87) PCT Pub. No.: WO2011/032330
PCT Pub. Date: Mar. 24, 2011

(65) Prior Publication Data
US 2012/0045427 A1 Feb. 23, 2012

(30) Foreign Application Priority Data
Sep. 18, 2009 (CN) .......................... 2009 1 0183359

(51) Int. Cl.
*C12N 1/20* (2006.01)
*A01N 63/00* (2006.01)

(52) U.S. Cl.
USPC ................. 435/252.4; 435/252.5; 435/833; 435/834; 504/117; 424/93.4; 424/93.46; 424/114

(58) Field of Classification Search
None
See application file for complete search history.

(56) References Cited

U.S. PATENT DOCUMENTS

| 6,318,023 | B1 * | 11/2001 | Yamashita | 504/117 |
| 7,442,224 | B2 * | 10/2008 | Porubcan | 71/6 |

FOREIGN PATENT DOCUMENTS

| CN | 1415737 | A | 5/2003 |
| CN | 1590535 | A | 3/2005 |
| CN | 1236051 | C | 1/2006 |
| CN | 101186887 | A | 5/2008 |
| CN | 101250495 | A | 8/2008 |
| CN | 100500005 | C | 6/2009 |
| CN | 101485336 | A | 7/2009 |
| CN | 101503659 | A | 8/2009 |
| CN | 101575574 | A | 11/2009 |
| JP | 9002911 | A | 1/1997 |

OTHER PUBLICATIONS

Tsai et al. Bulletin of Taichung District Agricultural Improvement Station, Jun. 2009, No. 103, pp. 53-62.*
Sun et al., "Antagonistic Rhizobacteria Strain *Bacillus subtilis* S 1 Against Banana *Fusarium* Wilt", Chinese Journal of Biological Control, 24(2)143-147 (May 2008).
Nel et al., "The Potential of Nonpathogenic *Fusarium oxysporum* and Other Biological Control Organisms for Supressing *Fusarium* Wilt of Banana", Plant Pathology, 55:217-223 (2006).
Lin et al., "Test on the Control Efficacy of Antagonistic Microorganism on Watermelon Wilt Disease" Journal of Guangxi Agric. and Biol. Science, 21(4):242-244 (Dec. 2002).
Zhu et al., "Effect of Biocontrol Strain ANTI-8098A of *Bacillus cereus* on Pathogenicity of *Ralstonia solanacearum*", Chinese journal of biological control, 25(1):41-47 (2009).
Yi et al., "Isolation and Identification of Endophytic *Brevibacillus brevis* and its Biocontrol Effect Against Tobacco Bacterial Wilt", Acta Phytopathologica Sinica, 37(3):301-306 (2007).
Ramesh et al., "Pseudomonads: Major Antagonistic Endophytic Bacteria to Suppress Bacterial Wilt Pathogen, *Ralstonia solanacearum* in the Eggplant (*Solanum melongena* L.)", World J. Microbiol Biotechnol., 25:47-55 (2009).

* cited by examiner

*Primary Examiner* — Vera Afremova
(74) *Attorney, Agent, or Firm* — Knobbe, Martens, Olson & Bear, LLP

(57) ABSTRACT

The present invention relates to the antagonistic bacteria that are used to prevent and eliminate tobacco bacterial wilt and their microbial organic fertilizer, which belong to the technology for agricultural intensive production. The present invention separates two antagonistic bacteria (*Brevibacillus brevis* NJL-25 and *Bacillus cereus* NJL-14) that have remarkable antagonistic action against the pathogens of tobacco bacterial wilt. Microbial organic fertilizer is produced from these antagonistic bacteria and organic compost. Wherein, the content of each of NJL-25 and NJL-14 is above $1 \times 10^{10}$ cfu/g, the content of total nitrogen is 4~5% (above 90% of the nitrogen is organic nitrogen), the content of total nitrogen-phosphorus-kalium nutrient is 6~10% and the content of organic matter is 30~35%. As indicated by experiments, after the microbial organic fertilizer is applied into soil, it will enable rapid multiplication of the antagonistic bacteria into a dominant microflora in the soil and achieve more than 97.6% of biocontrol rate of tobacco bacterial wilt in the soil suffering from tobacco bacterial wilt. If the microbial organic fertilizer is applied in the soil without continuous cropping obstacle in a long time, it can prevent the occurrence of the bacterial wilt of continuous cropping tobacco to a great extent.

3 Claims, 1 Drawing Sheet

CK1 CK2 T1 T4 T2 T3 T7 T5 T6   CK1 CK2 T1 T7 T5 T6

ANTAGONISTIC BACTERIA FOR PREVENTING AND ELIMINATING THE BACTERIAL WILT OF CONTINUOUS CROPPING TOBACCO AND THEIR MICROBIAL ORGANIC FERTILIZER

BACKGROUND OF THE INVENTION

1. Field of the Invention

The present invention relates to the antagonistic bacteria that can be used to prevent and eliminate the bacterial wilt of continuous cropping tobacco and their microbial organic fertilizer, which belong to the technology for agricultural intensive production and is exclusively used to overcome and eliminate the bacterial wilt of continuous cropping tobacco.

2. Description of the Related Art

Tobacco is the main economic crop in China, and its quality is related to the national economy and people's livelihood. Tobacco bacterial wilt is one of the major diseases of tobacco, which does serious harm and is called "cancer of tobacco". It was first found in the USA in 1880. Currently, it universally occurs in the tobacco producing areas in Southwest China and is often in a form of outbreak epidemic in the affected areas, resulting in devastating loss and about 80% of loss of yield in serious cases. Tobacco bacterial wilt is a serious soilborne bacterial disease. It is widely distributed in the tropical zone, subtropical zone and some warm areas in the world. In China, the disease occurs universally in Henan, Shandong, Jiangsu, Yunnan, Guangxi, Hebei, Hunan, Guangdong and Fujian and becomes one of the reasons for the decline of Chinese tobacco yield and quality. The pathogen of tobacco bacterial wilt (*Ralstonia solanacearum*) can be spread through soil, flowing water (for example, irrigation), seeds and other means and is highly adaptable to the environment. In the early stage of the infection of *Ralstonia solanacearum* to soil, as its quantity is small, the plants have the following symptoms: the growth is restricted and the plants are short, small, malformed and susceptible. Farmers often consider the symptoms as a problem of lacking nutrient and thus apply more nitrogen fertilizer. Consequently, the imbalance of the microfloras in the soil is from bad to worse, and the pathogen occupies a dominant position in rhizosphere, thus tobacco bacterial wilt occurs. Under the condition of high temperature and high humidity, the disease develops rapidly, and the morbidity in the fields with serious attack of the disease is 100%, resulting in no harvest.

On the other hand, the straw of paddy, wheat, corn, rape and other crops is burned on the spot and the excrement of the livestock and poultry raised on a scale is discarded. It not only seriously pollutes environment but also is a great waste of the raw material that can be used to produce organic fertilizer and bio-organic fertilizer products; enormous nutritive resources (C, N, P, K, S and trace elements) are lost outside the soil—plant system and the capability of sustainable development of Chinese agriculture is obviously weakened. How to maximally return the nutritive elements taken away from soil due to harvesting of crops to the soil? The only way is to make these solid organic wastes into commercial organic fertilizer and apply the fertilizer to the soil. If these solid organic wastes are synthesized into high-grade organic compost through high-temperature fermentation and then the compost is used as a carrier of functional bacteria to prepare microbial organic fertilizer, the function will be clear and there will be a good application prospect.

SUMMARY OF THE INVENTION

Technical Problem

The purpose of the present invention is to develop an antagonistic microbial organic fertilizer that can prevent and eliminate tobacco bacterial wilt. The prevention and cure rate of the fertilizer is above 80%. It can biologically restore the soil with continuous cropping obstacle and ensure the smooth development of intensive agriculture.

Technical Solution

The antagonistic bacteria that are used to prevent and eliminate the bacterial wilt of continuous cropping tobacco include strain NJL-25 and strain NJL-14, wherein, Strain NJL-25 belongs to *Brevibacillus brevis* and was collected by China General Microbiological Culture Collection Center (CGMCC) on Jul. 9, 2009. Its culture collection number is CGMCC No. 3175. Its main biological characteristics: Gram-positive; cells are in a shape of rod; the inflated sporocyst contains oval spores; the colonies are smooth and grow strictly under aerobic condition; catalase is negative; V.P. reaction is negative; methyl red test is negative; the fermentation of sucrose, fructose, mannitol and sorbitol generates acid but no gas; nitrate reductase is negative; starch hydrolysis is negative; glutin hydrolysis is positive; decomposition of casein is positive and doesn't generate hydrogen sulfide but generates indole; the optimum growth temperature is 30° C. and the optimum pH value is 7.0;

Strain NJL-14 belongs to *Bacillus cereus* and was collected by CGMCC on Jul. 10, 2009. Its culture collection number is CGMCC No. 3174. Its main biological characteristics: Gram-positive; cells are in a shape of rod; the sporocyst doesn't have obvious inflation; spores are round or cylindrical; and it is central spore or is close to central spore; the surface of colony is coarse, flat and irregular; it grows under facultative aerobic condition; the catalase is positive; V.P. reaction is positive; methyl red test is positive; the fermentation of glucose, sucrose, fructose, maltose and sorbitol generates acid but no gas; nitrate reductase is positive; starch hydrolysis is positive; glutin hydrolysis is positive; decomposition of casein is positive and doesn't generate hydrogen sulfide or indole; the optimum growth temperature is 30° C. and the optimum pH value is 7.0.

The microbial organic fertilizer for preventing and eliminating the bacterial wilt of continuous cropping tobacco, which is produced from the above-mentioned antagonistic bacteria, is characterized in that in the fertilizer, the content of each of the antagonistic bacteria NJL-25 and NJL-14 is above $1 \times 10^{10}$ cfu/g, total nitrogen is 4~5% (weight percent), above 90% (weight percent) of the total nitrogen is organic nitrogen, total nitrogen-phosphorus-kalium nutrient is 6~10% (weight percent) and organic matter is 30~35% (weight percent).

The microbial organic fertilizer that prevents and eliminates the bacterial wilt of continuous cropping tobacco is produced by the following method:

1) Strain NJL-25 and strain NJL-14 is respectively incubated in potato-dextrose-agar (PDA) culture to conduct liquid fermentation production under the following conditions: the initial range of pH value is 7.0-7.2, the culture temperature is 30° C., dissolved oxygen (DO): ventilation range is 30~100%, 170 rpm, spores are formed in the middle and late stage of the fermentation, the quantity of bacteria or spores in the fermented antagonist liquor is $\geq 1 \times 10^{10}$ cfu/mL; the preparation method of the used PDA culture (taking the preparation of 1 L of culture medium for example) are as follows: Unpeel 200 g of potato, cut it into small dices, boil it in water, boil it in boiling water for 30 min, filter the mixture, add 20 g of common sucrose into the filtrate, fix the volume at 1000 mL, adjust pH value to 7.2-7.4, and sterilize the liquor at 121° C. for 20 min.

2) NJL-25 and NJL-14 liquid microbial agents are respectively incubated to mature pig excrement compost and the mixture from microbial enzymatic hydrolysis of rapeseed meal at a dosage of 50 L/t. to conduct solid fermentation. The fermentation temperature is 30-50° C. During the fermentation, the material is turned over once a day. The fermentation is completed in 5-7 days to ensure the content of antagonistic bacteria is above $1\times10^8$ cfu/g. In the end, the solid microbial agents of antagonist NJL-25 and NJL-14 are obtained; the germination index of the mature pig excrement compost is more than 98%, the content of organic matter is $\geq$35%, the content of organic nitrogen is 1.2-2% and water content is 25-30%.

3) By two types—compost and the mixture from microbial decomposition of rapeseed meal, antagonist NJL-25 solid microbial agents and antagonist NJL-14 solid microbial agents are mixed at a volume ratio of 1:1 to obtain the mixed solid microbial agents of compost and the mixed solid microbial agents of the mixture from microbial decomposition of rapeseed meal.

4) The mixed solid microbial agents of compost (50-70% v/v) and the mixed solid microbial agents of the mixture from microbial enzymatic hydrolysis of rapeseed meal (30-50% v/v) are thoroughly mixed. The above-mentioned mixture is ripened for 2-3 days. During the ripening, it is turned over twice. In the end, the microbial organic fertilizer is evaporated at temperature of not above 60° C. till its water content is less than 30%. After packaging, the microbial organic fertilizer that prevents and eliminates the bacterial wilt of continuous cropping tobacco is obtained.

The microbial organic fertilizer can be exclusively used to prevent and eliminate the bacterial wilt of continuous cropping tobacco.

Beneficial Effects

The present invention relates to the microbial organic fertilizer that can overcome or eliminate the bacterial wilt of continuous cropping tobacco and its producing method. The pig excrement compost and the amino acid mixture from enzymatic hydrolysis of rapeseed meal are mixed with antagonistic bacteria solution to produce the microbial organic fertilizer. Comparing with the products in the current market, the product has the following advantages:

1) The fertilizer product contains two specific high-performance strains (*Brevibacillus brevis* and *Bacillus cereus*) that inhibit the growth of pathogenic bacteria of tobacco bacterial wilt. The inhibition effect is very remarkable. The experiment result indicates that after the product is applied to the soil suffering from the bacterial wilt of continuous cropping tobacco, the biocontrol rate of tobacco bacterial wilt is above 80%, and the biocontrol rate of bacterial wilt in the soil applied with the fertilizer in three consecutive years is even higher.

2) The fertilizer is organic fertilizer and contains rich organic matter (content is 30-35%) and the content of organic nitrogen is 4%, mostly of which is amino acids and micromolecule peptides. The content of total phosphor in the product is 4%. Moreover, the product has brilliant bioavailability. After the product is used, crops can smoothly get through phosphorin sensitive period in seedling stage. In comparison, after phosphoric fertilizer is applied to soil, the bioavailability is poor. The rich nutrition in organic fertilizer also provides a condition for the growth and multiplication of the antagonistic bacteria in the fertilizer so that it can survive in soil and form a dominant microflora, thus playing a role in preventing disease.

3) As it is a bio-strain preparation, it doesn't have any problem caused by the use of chemical pesticides and is conducive to the pollution-free production of tobacco. Farmers may not use or reduce the dosage of other chemical pesticides that prevent and cure bacterial wilt. This not only can reduce farmers' expenditure but also can improve the quality of agricultural products. Meanwhile, the microbial fertilizer has the function of increasing yield, thus farmers' revenue can be increased.

A: Inhibition zone of antagonist NJL-25 B: Inhibition zone of antagonist NJL-14

Figure 2:
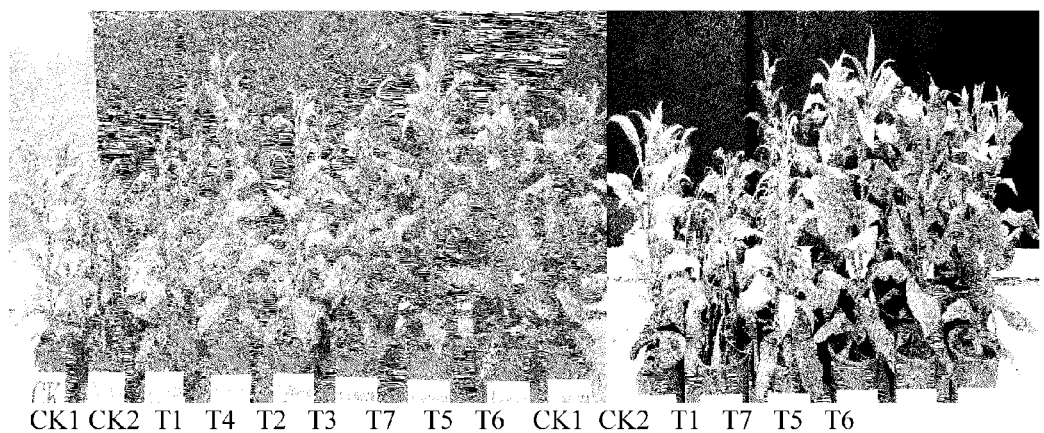

FIG. 2: Prevention and cure effect in greenhouse pot experiment

Figure 1:
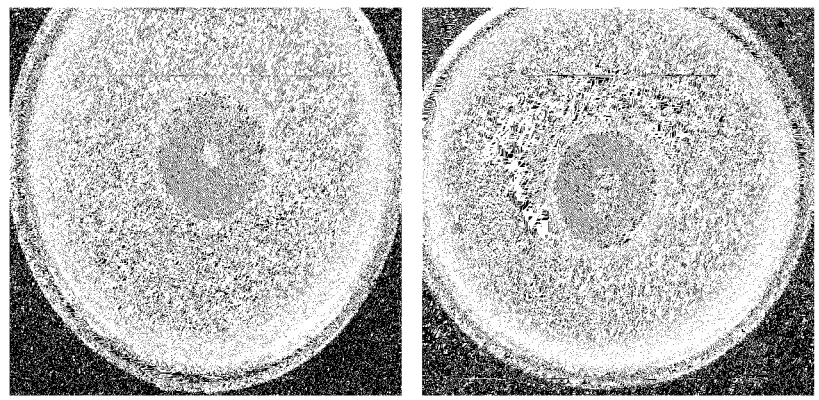
FIG. 1: Inhibition zones of antagonistic bacteria NJL-25 and NJL-14

DETAILED DESCRIPTION OF THE PREFERRED EMBODIMENT (I) Strain Separation and Identification Samples of the plants with continuous cropping obstacle and serious symptoms of bacterial wilt as well as the surrounding soil are collected and stored at low temperature. Kelman's TTC Agar selective culture medium is adopted to separate pathogen—*Ralstonia solanacearum*. Then the pathogenic bacteria of wilt are used as an indicator, and the antagonistic bacteria are separated from the rhizosphere soil of healthy tobacco plants in the field for continuous cropping of tobacco suffering from bacterial wilt. In the end, through pot experiment and field experiment, high-performance antagonistic strains NJL-25 and NJL-14 are obtained by means of secondary screening. The strains are identified. They are stored in 30% glycerin at −70° C. The diameter of the inhibition zone of antagonist NJL-25 is 24 mm and that of NJL-14 is 29 mm (FIG. 1).

Strain NJL-25 belongs to *Brevibacillus brevi*. Its main biological characteristics: Gram-positive; cells are in a shape of rod; the inflated sporocyst contains oval spores; the colonies are smooth and grow strictly under aerobic condition; catalase is negative; V.P. reaction is negative; methyl red test is negative; the fermentation of sucrose, fructose, mannitol and sorbitol generates acid but no gas; nitrate reductase is negative; starch hydrolysis is negative; glutin hydrolysis is positive; decomposition of casein is positive and doesn't generate hydrogen sulfide but generates indole; the optimum growth temperature is 30° C. and the optimum pH value is 7.0;

Strain NJL-14 belongs to *Bacillus cereus*. Its main biological characteristics: Gram-positive; cells are in a shape of rod; the sporocyst doesn't have obvious inflation; spores are round or cylindrical; and it is central spore or is close to central spore; the surface of colony is coarse, flat and irregular; it grows under facultative aerobic condition; the catalase is positive; V.P. reaction is positive; methyl red test is positive; the fermentation of glucose, sucrose, fructose, maltose and sorbitol generates acid but no gas; nitrate reductase is positive; starch hydrolysis is positive; glutin hydrolysis is positive; decomposition of casein is positive and doesn't generate hydrogen sulfide or indole; the optimum growth temperature is 30° C. and the optimum pH value is 7.0.

(II) Production of the Bacterial Preparations

1) Strain NJL-25 and NJL-14 is respectively incubated to PDA culture to conduct liquid fermentation production under the following conditions: the initial pH range is 7.0-7.2, the culture temperature is 30° C., DO: ventilation range is 30~100%, 170 rpm, spores are formed in the middle and late stage of the fermentation, the quantity of bacteria or spores in the fermented antagonist liquor is $\geq 1\times 10^{10}$ cfu/mL;

Preparation method of the used PDA culture (taking the preparation of 1 L of culture medium for example): Unpeel 200 g potato, cut it into small dices and boil it in boiling water for 30 min, then filter the mixture, add 20 g of common sucrose into the filtrate, fix the volume at 1000 mL, adjust pH value to 7.2-7.4, and sterilize the liquor at 121° C. for 20 min.

2) NJL-25 and NJL-14 liquid microbial agents are respectively incubated to mature pig excrement compost and the mixture from microbial enzymatic hydrolysis of rapeseed meal at a dosage of 50 L/t. to conduct solid fermentation. During the fermentation, the material is turned over once a day to ensure the temperature of solid fermentation is 30-50° C. The fermentation is completed in 5-7 days to ensure the content of antagonist is above $1\times 10^8$ cfu/g. In the end, the solid microbial agents of antagonist NJL-25 and NJL-14 are obtained; the germination index of the mature pig excrement compost is more than 98%, the content of organic matter is $\geq 35\%$ (weight percent), the content of organic nitrogen is 1.2-2% (weight percent) and water content is 25-30% (weight percent).

The mixture from microbial decomposition of rapeseed meal is produced by the following method (known and used by the public, see Chinese invention patent ZL200610086126.0, a biological preparation method of amino acids for agricultural use and their fertilizer product): add the fermentation liquor of strain 37-1 into raw material rapeseed meal, adjust water content to 55-65% and pH value to 6.0-7.5, conduct open solid fermentation, turn it over once the fermentation temperature rises to 50° C., turn it over every day since then, and maintain the temperature at 35-50° C. for 5 days. After solid fermentation starts, the pH value of the material will keep rising. Whenever it is turned over, acidic liquid should be added to adjust water content and pH value and maintain water content at 55-65% and pH value at 6.0-7.0. When fermentation is terminated, acidic liquid will be sprayed again till pH value of the material is about 5.0. After that, the material is dried at low temperature or by air. The final product is the mixture from microbial decomposition of rapeseed meal (mixture containing amino acids).

3) By two types—compost and the mixture from microbial decomposition of rapeseed meal, antagonist NJL-25 solid microbial agents and antagonist NJL-14 solid microbial agents are mixed at a volume ratio of 1:1 to obtain the mixed solid microbial agents of compost and the mixed solid microbial agents from the mixture of microbial decomposition of rapeseed meal.

4) The individual-bacterium or mixed-bacteria solid microbial agents of compost (70% v/v) and the mixed solid microbial agents of the mixture from microbial enzymatic hydrolysis of rapeseed meal (30% v/v) are thoroughly mixed. The mixture is ripened 2-3 day. During the ripening, it is turned over twice. In the end, the microbial organic fertilizer is evaporated at temperature of not above 60° C. till its water content is less than 30%. The individual-bacterium microbial organic fertilizer (containing strain NJL-25 and NJL-14, respectively) and mixed microbial organic fertilizer that prevent and eliminate the bacterial wilt of continuous cropping tobacco will be obtained.

In the mixed microbial organic fertilizer produced from the above antagonistic bacteria (the microbial organic fertilizer exclusively used to prevent and eliminate the bacterial wilt of continuous cropping tobacco), the content of each of antagonistic bacteria NJL-25 and NJL-14 is above $1\times 10^{10}$ cfu/g, the content of total nitrogen is 4~5% (weight percent), above 90% of the total nitrogen is organic nitrogen, total nitrogen-phosphorus-kalium nutrient is 6~10% (weight percent) and organic matter is 30~35% (weight percent).

(III) Greenhouse Pot Experiment

The experimental soil is the soil for continuous cropping of tobacco, with serious bacterial wilt. The tobacco seeds adopted are "Yun Yan 97" that is sensitive to tobacco bacterial wilt. The treatment is as follows:

$CK_1$: Healthy paddy soil; $CK_2$: Soil for continuous cropping of tobacco; T1: CK2+amino acid organic fertilizer; T2: $CK_2$+NJL-25 fermentation liquor; T3: $CK_2$+NJL-14 fermentation liquor; T4: CK2+Mixture of NJL-14 and NJL-25 fermentation liquors (1:1); T5: CK2+NJL-25 microbial organic fertilizer; T6: CK2+NJL-14 microbial organic fertilizer; T7: CK2+NJL-14 and NJL-25 mixed microbial organic fertilizer.

Each treatment is repeated four times. Each repetition uses 23 kg sick soil per pot. Antagonistic bacteria are incubated to ensure the concentration of the antagonistic bacteria in soil reaches $10^8$ cfu/g of dry soil. In T5-T7, 115 g microbial organic fertilizer is applied in each pot. Chemical fertilizer is used to make up the difference of fertility. Before tobacco seedlings are transplanted, they are soaked in bacterial suspension for 30 min. The morbidity is recorded 10 days after incubation. After 25 days, the morbidity of CK2 is 100%, whereas the incubation of antagonist liquor or microbial organic fertilizer can effectively reduce the morbidity of bacterial wilt. The mixed microbial organic fertilizer produced from NJL-14 and NJL-25 has the best prevention and cure effect (FIG. 2) with morbidity of 0%.

The application of antagonistic bacteria can not only prevent and cure tobacco bacterial wilt, greatly reduce the quantity of *R. solanacearum* in soil, promote the changes of the microflora at rhizosphere of tobacco, remarkably increase beneficial bacterial flora, and remarkably reduce harmful fungal and pathogenic floras (Table 1), but also can remarkably increase the biomass of tobacco (Table 2). The application of antagonistic bacteria, particularly the application of microbial organic fertilizer shows a remarkable difference from CK1 and CK2 in terms of biomass. Microbial organic fertilizer has a better biocontrol effect than that of liquid bacterial preparations (biomass increases to 1.65 folds).

After antagonistic bacteria are applied, the systematic disease resistance of tobacco is enhanced to some extent as well as the activity of related enzymes is raised significantly. It is probable that the addition of antagonistic bacteria leads to the generation of systematic resistance of tobacco plants (Table 3).

(IV) Field Experiment

Microbial organic fertilizer was applied to the field that was seriously attacked by tobacco bacterial wilt at Bojian Village, Huangdu Township, Xuancheng City, Anhui Province in 2009.

Treatment of field experiment: 1. Apply local compound fertilizer exclusively for tobacco; 2. Apply the mixed microbial organic fertilizer produced from NJL-14 and NJL-25. The field suffering from serious bacterial wilt is randomly arranged into four repetitions. Each repetition has two treatments. There are 8 plots in total. The tobacco variety is local popular variety "Yun Yan 97". Both tobacco seedlings and fertilizer adopt hole application. The dosage of bio-organic fertilizer is 30 kg/mu. Chemical fertilizer is used to make up the fertility difference between treatment 1 and treatment 2.

Data are collected from the field on a regular basis. Statistics on morbidity, disease index and microfloras is conducted. After final harvesting, the difference of biomass among different treatments is calculated. The application of the microbial organic fertilizer with mixed antagonistic bacteria can remarkably reduce the occurrence of bacterial wilt, and the controlling rate of above 97.6% can be achieved as well as the yield of tobacco leaves was increased by 2.27 times (Table 4).

The present invention proceeds from microflora, and develops a microbial organic fertilizer product that can remarkably eliminate the occurrence of the bacterial wilt of continuous cropping tobacco and achieve the controlling rate of above 97.6% (the field experiment in Anhui). The mechanism of the fertilizer product is that the functional bacteria and their active carbon and nitrogen sources provided by the fertilizer product provide a very good condition for the cultivation of beneficial microflora in the soil with continuous cropping obstacle, and enable the soil to quickly restore and establish the ecology and food chain of exogenous functional bacterial organisms; on the other hand, the fertilizer product has a high content of organic nitrogen and organic phosphor. These nutritive substances are beneficial to the growth of the crops in the soil with continuous cropping obstacle and greatly improve the seedling standing rate and tolerance of tobacco.

TABLE 1

Differences between microbe content on root surface of the potted tobacco under different treatment

| Treatment/ quantity (cfu/g of soil) | Pathogen | Antagonistic bacteria | Bacteria | Actinomyces | Fungi |
|---|---|---|---|---|---|
| CK1 | $3.8 \times 10^3$ | $7.9 \times 10^5$ | $2.1 \times 10^8$ | $5.5 \times 10^5$ | $4.8 \times 10^4$ |
| CK2 | $2.2 \times 10^7$ | $4.6 \times 10^4$ | $5.4 \times 10^8$ | $3.3 \times 10^4$ | $6.1 \times 10^5$ |
| T1 | $5.8 \times 10^3$ | $2.6 \times 10^4$ | $5.2 \times 10^8$ | $4.9 \times 10^7$ | $3.8 \times 10^4$ |
| T2 | $6.9 \times 10^4$ | $3.0 \times 10^6$ | $5.1 \times 10^8$ | $7.1 \times 10^5$ | $7.1 \times 10^3$ |
| T3 | $3.7 \times 10^4$ | $2.7 \times 10^7$ | $6.9 \times 10^8$ | $5.2 \times 10^6$ | $4.9 \times 10^3$ |
| T4 | $4.4 \times 10^4$ | $4.3 \times 10^6$ | $6.0 \times 10^8$ | $3.7 \times 10^7$ | $5.9 \times 10^3$ |
| T5 | $6.5 \times 10^4$ | $5.0 \times 10^7$ | $2.2 \times 10^8$ | $5.0 \times 10^5$ | $7.7 \times 10^3$ |
| T6 | $7.3 \times 10^4$ | $3.8 \times 10^7$ | $6.9 \times 10^8$ | $7.7 \times 10^5$ | $5.0 \times 10^3$ |
| T7 | $9.4 \times 10^3$ | $8.2 \times 10^7$ | $2.1 \times 10^9$ | $8.3 \times 10^5$ | $4.4 \times 10^3$ |

TABLE 2

Differences between fresh weight and dry weight of the potted tobacco under different treatment

| Treatment/ biomass | Fresh weight of aboveground part (g) | Fresh weight of root (g) | Dry weight of aboveground part (g) | Dry weight of root (g) |
|---|---|---|---|---|
| CK1 | 352.29 ± 18.02a | 57.13 ± 2.63b | 53.68 ± 1.70b | 16.84 ± 1.17b |
| CK2 | 262.53 ± 9.64b | 49.94 ± 8.22a | 36.60 ± 0.50a | 8.22 ± 1.03a |
| T1 | 490.34 ± 10.98cd | 64.57 ± 1.62c | 57.91 ± 0.92c | 22.42 ± 0.23d |
| T2 | 448.62 ± 19.91c | 84.03 ± 4.92e | 70.93 ± 2.72d | 19.42 ± 1.16c |
| T3 | 450.90 ± 13.69c | 100.49 ± 0.53g | 58.01 ± 1.10d | 19.42 ± 0.72c |
| T4 | 537.03 ± 10.11d | 76.98 ± 0.24d | 71.99 ± 1.21d | 22.82 ± 0.93d |
| T5 | 742.10 ± 12.49e | 91.44 ± 0.54f | 94.19 ± 2.10f | 20.79 ± 1.68cd |
| T6 | 733.30 ± 10.09e | 83.73 ± 1.15e | 87.43 ± 2.68e | 19.65 ± 1.51c |
| T7 | 756.87 ± 18.63e | 97.78 ± 0.60fg | 86.68 ± 0.42f | 25.53 ± 1.55e |

TABLE 3

Changes of the systematic resistance enzymes and the enzymes relating to secondary metabolites in the aboveground part under different treatment

| | Activity of the enzymes in the aboveground part | | | | | |
|---|---|---|---|---|---|---|
| Treatment | POD [u/(g·min)] | CAT (u/gFW/min) | SOD [units/g(Fw)] | PPO (0.01 A/min) | PAL (0.01 A/min) | APX [ΔA290/(gFW·h)] |
| CK1 | 1208.33 | 825.32 | 125.77 | 26.00 | 126.54 | 14.92 |
| CK2 | 1863.37 | 879.81 | 187.22 | 6.33 | 105.66 | 7.22 |
| T1 | 1056.11 | 706.73 | 167.34 | 14.33 | 63.60 | 12.36 |
| T2 | 1425.00 | 307.19 | 115.81 | 11.00 | 62.64 | 16.04 |
| T3 | 1325.40 | 375.79 | 119.45 | 15.33 | 35.56 | 11.57 |
| T4 | 841.42 | 545.75 | 119.53 | 9.67 | 56.67 | 16.55 |
| T5 | 941.67 | 146.67 | 127.66 | 3.00 | 104.62 | 12.18 |
| T6 | 592.11 | 64.10 | 113.56 | 11.67 | 67.06 | 11.58 |
| T7 | 552.88 | 166.67 | 21.98 | 36.33 | 3.33 | 17.32 |

TABLE 4

Effect of the field experiment in Anhui

| Treatment/related data | Total yield (kg) | Average yield of a plot | Morbidity | Disease index (infection index) |
|---|---|---|---|---|
| Common compound fertilizer | 112.93 | 28.2325 | 52.7 | 45.5 |

TABLE 4-continued

Effect of the field experiment in Anhui

| Treatment/related data | Total yield (kg) | Average yield of a plot | Morbidity | Disease index (infection index) |
|---|---|---|---|---|
| Bio-organic fertilizer | 369.07 | 92.2675 | 3.1 | 2.1 |

Note:
Disease prevention rate = 100 × (disease index of control group − disease index of treatment group)/disease index of control group Industrial standard for classification of tobacco disease: level 0: the entire plant has no disease. Level 1: There are sporadic chlorotic spots on stem, or a minority of the laminae on the side with streak withers. Level 2: Black streaks appear on stem, but they haven't developed to the top, or more than one-half of the laminae on the infected side withers. Level 3: Level 4: The infected plant generally dies.

What is claimed is:

1. A microbial organic fertilizer for controlling bacterial wilt of continuous cropping tobacco comprising: antagonistic bacteria, wherein said antagonistic bacteria comprise *Brevibacillus brevis* strain NJL-25 and *Bacillus cereus* strain NJL-14, both of which are deposited under identification numbers CGMCC 3175 and 3174, respectively.

2. The microbial organic fertilizer according to claim 1, wherein a content of each of the antagonistic bacteria NJL-25 and NJL-14 is above $1 \times 10^{10}$ colony-forming unit (cfu)/per 1 gram of the fertilizer, a content of total nitrogen is 4~5% (eight percent of a total weight of the fertilizer, wherein above 90% weight percent of the total weight of said nitrogen is organic nitrogen, and 6~10% weight percent of the total weight of said nitrogen is nitrogen-phosphorus-kalium; and wherein a portion of organic matter in the fertilizer is 30~35% weight percent of the total weight of the fertilizer.

3. A method of controlling bacterial wilt of continuous cropping tobacco comprising:

applying the microbial organic fertilizer according to claim 1 to an area that is in need of such controlling.

* * * * *

UNITED STATES PATENT AND TRADEMARK OFFICE
CERTIFICATE OF CORRECTION

PATENT NO.        : 8,476,057 B2
APPLICATION NO.   : 12/747508
DATED             : July 2, 2013
INVENTOR(S)       : Shen et al.

Page 1 of 1

It is certified that error appears in the above-identified patent and that said Letters Patent is hereby corrected as shown below:

Title Page:

In column 2 (page 1 item 56) at line 14, Under Other Publications, Change "Supressing" to --Suppressing--.

In the Specification:

In column 2 at line 27, Change "glutin" to --gluten--.

In column 2 at line 42, Change "glutin" to --gluten--.

In column 4 at line 55, Change "glutin" to --gluten--.

In column 5 at line 2, Change "glutin" to --gluten--.

In the Claims:

In column 10 at line 8, In Claim 2, Change "(cfu)/" to --(cfu)--.

In column 10 at line 10 (approx.), In Claim 2, Change "(eight" to --weight--.

Signed and Sealed this
Eighteenth Day of March, 2014

Michelle K. Lee
*Deputy Director of the United States Patent and Trademark Office*